US012141948B2

(12) United States Patent
Ohtsuka et al.

(10) Patent No.: US 12,141,948 B2
(45) Date of Patent: Nov. 12, 2024

(54) DENTITION IMAGE CAPTURING SYSTEM AND DENTITION IMAGE CAPTURING METHOD

(71) Applicant: Panasonic Intellectual Property Management Co., Ltd., Osaka (JP)

(72) Inventors: Yoshio Ohtsuka, Osaka (JP); Masato Izawa, Osaka (JP); Tomoki Ogawa, Osaka (JP); Toshiyuki Nakashima, Nara (JP); Masayuki Aihara, Osaka (JP); Kazuhiro Funamoto, Hyogo (JP); Tadashi Miki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 35 days.

(21) Appl. No.: 18/030,445

(22) PCT Filed: Nov. 24, 2021

(86) PCT No.: PCT/JP2021/042961
§ 371 (c)(1),
(2) Date: Apr. 5, 2023

(87) PCT Pub. No.: WO2022/113995
PCT Pub. Date: Jun. 2, 2022

(65) Prior Publication Data
US 2023/0377101 A1 Nov. 23, 2023

(30) Foreign Application Priority Data
Nov. 27, 2020 (JP) .................................. 2020-197574

(51) Int. Cl.
*G06T 5/77* (2024.01)
*A61B 1/06* (2006.01)
(Continued)

(52) U.S. Cl.
CPC ............. *G06T 5/77* (2024.01); *A61B 1/0625* (2022.02); *A61B 1/24* (2013.01); *G06T 5/50* (2013.01);
(Continued)

(58) Field of Classification Search
CPC .. G06T 5/77; G06T 5/50; G06T 7/136; G06T 7/90; G06T 7/97; G06T 2207/20221;
(Continued)

(56) References Cited

U.S. PATENT DOCUMENTS 5,436,655 A * 7/1995 Hiyama ............. A61B 1/00194
348/45
2004/0042683 A1 * 3/2004 Hagisato ................. H04N 23/76
348/E5.037

(Continued)

FOREIGN PATENT DOCUMENTS

JP   2004-237081 A   8/2004
JP   2007-236707 A   9/2007
(Continued)

OTHER PUBLICATIONS

International Preliminary Report on Patentability dated Jun. 8, 2023 issued in International Patent Application No. PCT/JP2021/042961, with English translation.
(Continued)

*Primary Examiner* — Timothy R Newlin
(74) *Attorney, Agent, or Firm* — Rimon P.C.

(57) ABSTRACT

A dentition image capturing system includes: illumination devices to radiate light; an imaging device to capture first and second dentition images in a predetermined exposure period; a high luminance region extraction unit to extract a high luminance region for the first and second dentition images; a high luminance region comparison unit to calculate a degree of similarity between the high luminance
(Continued)

region of the first dentition image and the second dentition image; a halation region specification unit to specify the high luminance region of the first dentition image as a halation region in a case where the similarity degree is smaller than a predetermined threshold; an image synthesis processing unit executing image synthesis processing of extracting a trimming region in the second dentition image corresponding to the halation region and replacing the halation region with the trimming region; and a dentition image output unit to output the first dentition image.

8 Claims, 14 Drawing Sheets

(51) Int. Cl.
| | |
|---|---|
| *A61B 1/24* | (2006.01) |
| *G06T 5/50* | (2006.01) |
| *G06T 7/00* | (2017.01) |
| *G06T 7/136* | (2017.01) |
| *G06T 7/90* | (2017.01) |
| *H04N 17/00* | (2006.01) |
| *H04N 23/72* | (2023.01) |
| *H04N 23/74* | (2023.01) |
| *H04N 23/76* | (2023.01) |

(52) U.S. Cl.
CPC ............... *G06T 7/136* (2017.01); *G06T 7/90* (2017.01); *G06T 7/97* (2017.01); *H04N 17/002* (2013.01); *H04N 23/72* (2023.01); *H04N 23/74* (2023.01); *H04N 23/76* (2023.01); *G06T 2207/20221* (2013.01); *G06T 2207/30036* (2013.01)

(58) Field of Classification Search
CPC ........ G06T 2207/30036; A61B 1/0625; A61B 1/24; A61B 1/000094; A61B 1/00045; A61B 1/00096; A61B 1/00188; A61B 1/05; A61B 1/0607; A61B 1/0676; A61B 1/0684; H04N 17/002; H04N 23/72; H04N 23/74; H04N 23/76; H04N 23/743; H04N 23/56; H04N 23/71; H04N 23/73; H04N 23/80; A61C 9/0046; G03B 15/0405; G03B 15/14
See application file for complete search history.

(56) References Cited

U.S. PATENT DOCUMENTS

| | | | |
|---|---|---|---|
| 2005/0003323 A1 | 1/2005 | Katsuda et al. | |
| 2005/0140819 A1* | 6/2005 | Kawamura | H04N 23/73 348/E5.037 |
| 2008/0050109 A1* | 2/2008 | Noyes | H04N 23/71 396/234 |
| 2010/0123781 A1* | 5/2010 | Shimura | H04N 23/74 348/222.1 |
| 2010/0245551 A1* | 9/2010 | Morita | A61B 1/0655 348/E7.085 |
| 2011/0143307 A1* | 6/2011 | Takebayashi | A61C 11/00 433/74 |
| 2012/0075445 A1* | 3/2012 | Uchihara | H04N 7/183 348/241 |
| 2014/0063201 A1* | 3/2014 | Ohkoba | A61B 1/00009 348/48 |
| 2015/0219552 A1* | 8/2015 | Kanamori | G02B 21/365 356/369 |
| 2015/0355104 A1* | 12/2015 | Matsuda | G06T 7/586 356/237.2 |
| 2016/0089011 A1* | 3/2016 | Shiraishi | H04N 23/843 348/71 |
| 2017/0024859 A1* | 1/2017 | Schnitzler | G06T 7/97 |
| 2017/0195540 A1* | 7/2017 | Sambongi | H04N 25/772 |
| 2018/0101963 A1* | 4/2018 | Okawa | G06T 7/60 |
| 2018/0139345 A1* | 5/2018 | Goh | H04N 1/19594 |
| 2018/0225845 A1* | 8/2018 | Aarabi | G06T 5/94 |
| 2018/0242818 A1* | 8/2018 | Kubo | A61B 1/005 |
| 2018/0289240 A1* | 10/2018 | Aoyama | A61B 1/000094 |
| 2018/0352134 A1* | 12/2018 | Sun | H04N 23/741 |
| 2019/0150724 A1 | 5/2019 | Elazar et al. | |
| 2019/0320106 A1* | 10/2019 | Tatara | H04N 23/73 |
| 2020/0265635 A1* | 8/2020 | Endo | G06V 20/20 |

FOREIGN PATENT DOCUMENTS

| | | |
|---|---|---|
| JP | 2008-160519 A | 7/2008 |
| JP | 2010-124043 A | 6/2010 |
| JP | 2018-013740 A | 1/2018 |

OTHER PUBLICATIONS

International Search Report dated Feb. 8, 2022 issued in International Patent Application No. PCT/JP2021/042961, with English translation.
Extended European Search Report dated Apr. 18, 2024 issued in the corresponding European Patent Application No. 21897967.2.
Notice of Reasons for Refusal dated Apr. 23, 2023 issued in the corresponding Japanese Patent Application No. 2022-565368, with English translation.

* cited by examiner

DENTITION IMAGE

BP₁

DENTITION IMAGE CAPTURING SYSTEM AND DENTITION IMAGE CAPTURING METHOD

CROSS-REFERENCE OF RELATED APPLICATIONS

This application is the U.S. National Phase under 35 U.S.C. § 371 of International Patent Application No. PCT/JP2021/042961, filed on Nov. 24, 2021, which in turn claims the benefit of Japanese Patent Application No. 2020-197574, filed on Nov. 27, 2020, the entire disclosures of which Applications are incorporated by reference herein.

TECHNICAL FIELD

The present disclosure relates to a dentition image capturing system and a dentition image capturing method.

BACKGROUND ART

As means for observing inside of an oral cavity, an intraoral camera (Patent Document 1 and Patent Document 2) having a function of irradiating the inside of the oral cavity with light is disclosed in Patent Documents 1 and 2.

PRIOR ART DOCUMENTS

Patent Documents

Patent Document 1: JP 2004-237081 A
Patent Document 2: JP 2007-236707 A

SUMMARY OF THE INVENTION

Problems to be Solved by the Invention

Incidentally, when an oral cavity is irradiated with light and an image of a tooth is captured, there is a case where halation (so-called "whiteout") may occur due to specular reflection on a surface of the tooth as a result of the tooth being wet with saliva or blood or due to a metal inlay used for a treatment scar as well as the tooth being white and glossy. When halation occurs, an image of the tooth becomes unclear, and there is a possibility that a state of the tooth cannot be correctly confirmed.

It is therefore an object of the present disclosure to clearly capture an image of a tooth.

Means for Solving the Problems

In order to solve the above problem, according to one aspect of the present disclosure, there is provided a dentition image capturing system including:
  a plurality of illumination devices configured to irradiate a tooth to be captured with light from different directions;
  an imaging device configured to capture first and second dentition images including the tooth under different illumination conditions of the plurality of illumination devices in a predetermined exposure period;
  a high luminance region extraction unit configured to extract a high luminance region in which luminance exceeds a predetermined luminance threshold for each of the first and second dentition images;
  a high luminance region comparison unit configured to calculate a degree of similarity indicating a degree of similarity between a high luminance region of the first dentition image and a high luminance region of the second dentition image;
  a halation region specification unit configured to specify the high luminance region of the first dentition image as a halation region in a case where the degree of similarity is smaller than a predetermined similarity threshold;
  an image synthesis processing unit configured to extract a trimming region in the second dentition image corresponding to the halation region of the first dentition image and execute image synthesis processing of replacing the halation region with the trimming region; and
  a dentition image output unit configured to output the first dentition image subjected to image synthesis processing.

Further, according to another aspect of the present disclosure, there is provided a dentition image capturing method for capturing a dentition image including a tooth to be captured, the method including:
  irradiating a tooth to be captured with light from different directions by a plurality of illumination devices,
  capturing first and second dentition images including the tooth by an imaging device under different illumination conditions of the plurality of illumination devices in a predetermined exposure period;
  extracting a high luminance region in which luminance exceeds a predetermined luminance threshold for each of the first and second dentition images;
  calculating a degree of similarity indicating a degree of similarity between a high luminance region of the first dentition image and a high luminance region of the second dentition image;
  specifying the high luminance region of the first dentition image as a halation region in a case where the degree of similarity is smaller than a predetermined similarity threshold; extracting a trimming region in the second dentition image corresponding to the halation region;
  executing image synthesis processing of replacing the halation region with the trimming region; and
  outputting the first dentition image subjected to image synthesis processing.

Effects of the Invention

According to the present disclosure, an image of a tooth can be clearly captured.

MODES FOR CARRYING OUT THE INVENTION

Hereinafter, embodiments will be described in detail with reference to the drawings as appropriate. However, unnecessarily detailed description may be omitted. For example, detailed description of a well-known matter and repeated description of substantially the same configuration may be omitted. This is to avoid unnecessary redundancy of the following description and to facilitate understanding of those skilled in the art.

Note that the inventors provide the accompanying drawings and the following description in order for those skilled in the art to fully understand the present disclosure and do not intend to limit the subject matter described in the claims by the accompanying drawings and the following description.

Hereinafter, embodiments of the present disclosure will be described with reference to the drawings.

First Embodiment

Figure 1:
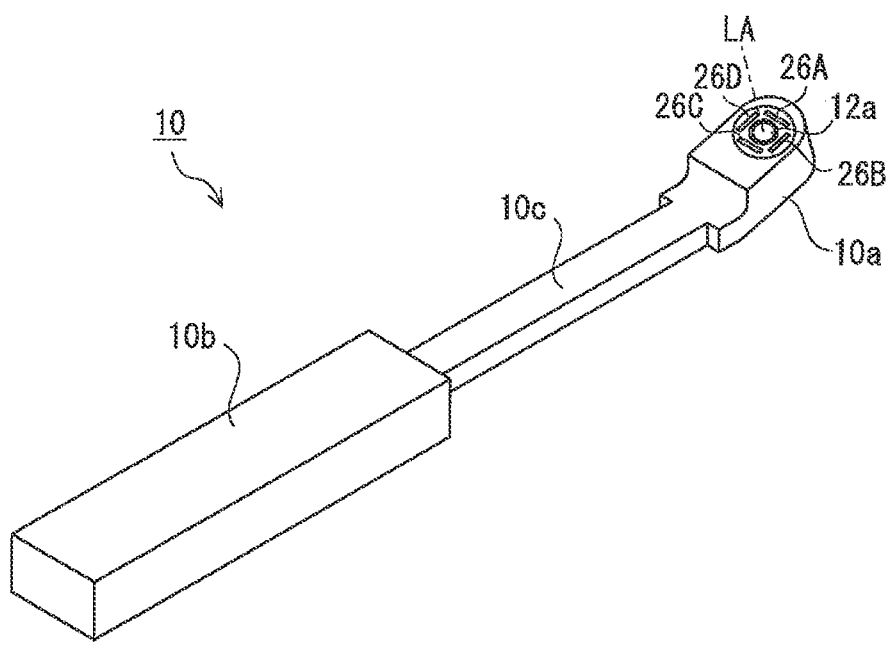
FIG. 1 is a perspective view of an intraoral camera in a dentition image capturing system according to a first embodiment of the present disclosure.
Figure 2:
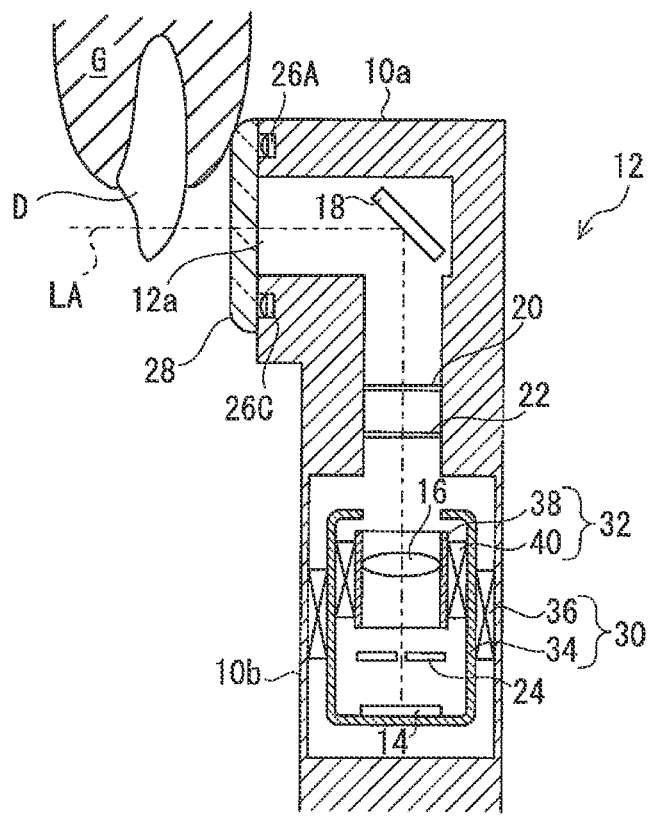
FIG. 2 is a cross-sectional view schematically illustrating an imaging optical system incorporated in the intraoral camera.

FIG. 1 is a perspective view of an intraoral camera in a dentition image capturing system according to a first embodiment of the present disclosure. FIG. 2 is a cross-sectional view schematically illustrating an imaging optical system incorporated in the intraoral camera.

As illustrated in FIG. 1, in a case of the first embodiment, an intraoral camera 10 includes a toothbrush-like casing that can be handled with one hand, and the casing includes a head portion 10a to be disposed in the oral cavity of the user during imaging of dentition, a handle portion 10b to be held by the user, and a neck portion 10c connecting the head portion 10a and the handle portion 10b.

As illustrated in FIG. 2, in the first embodiment, an imaging optical system 12 of the intraoral camera 10 is incorporated in the head portion 10a and the neck portion 10c. The imaging optical system 12 includes an imaging element 14 and a lens 16 disposed on an optical axis LA of the imaging optical system 12.

The imaging element 14 is, for example, an imaging device such as a C-MOS sensor and a CCD element, and an image of the tooth D is formed by the lens 16. The imaging element 14 outputs a signal (image data) corresponding to the formed image to the outside.

The lens 16 is, for example, a condenser lens and forms an incident image of the tooth D on the imaging element 14. Note that the lens 16 may be one lens or a lens group including a plurality of lenses.

In a case of the first embodiment, the imaging optical system 12 further includes a mirror 18 that reflects the image of the tooth D toward the lens 16, an infrared cut filter 20 and a complementary color filter 22 disposed between the mirror 18 and the lens 16, and a diaphragm 24 disposed between the lens 16 and the imaging element 14.

The mirror 18 is disposed on the optical axis LA of the imaging optical system 12 so as to reflect the image of the tooth D that has passed through an incidence port 12a of the imaging optical system 12 toward the lens 16.

The infrared cut filter 20 is a filter that cuts infrared light included in light incident on the imaging element 14. In a case where the filter of each color pixel (RGB) of the imaging element 14 such as a CCD element and a C-MOS sensor has total transparency, infrared light is recognized as white light. To address this, the infrared cut filter 20 cuts infrared light from light before being incident on the imaging element 14.

The complementary color filter 22 is a filter that selectively transmits light of a predetermined wavelength. The complementary color filter 22 selectively transmits light having a wavelength of, for example, 430 nm to 460 nm and cuts light having other wavelengths.

The diaphragm 24 is a plate-like member including a through hole on the optical axis LA of the imaging optical system 12 and achieves a deep focal depth. As a result, focus can be adjusted in a depth direction in the oral cavity, so that a dentition image with clear outline can be obtained. In a case of the first embodiment, the complementary color filter 22 is included in the imaging optical system 12, so that a fluorescent light beam is effectively processed by the diaphragm 24.

Furthermore, the intraoral camera 10 is equipped with a plurality of first to fourth LEDs 26A to 26D as illumination devices that irradiate the tooth D to be captured with light at the time of imaging. The first to fourth LEDs 26A to 26D are, for example, white LEDs. Further, as illustrated in FIG. 1, in a case of the first embodiment, the first to fourth LEDs 26A to 26D are disposed so as to surround the incidence port 12a. A translucent cover 28 that covers the first to fourth LEDs 26A to 26D and the incidence port 12a is provided in the head portion 10a so as to prevent the illumination light from becoming insufficient due to the gum G, or the like, abutting on the first to fourth LEDs 26A to 26D.

Furthermore, in a case of the present embodiment, as illustrated in FIG. 2, the intraoral camera 10 includes a composition adjustment mechanism 30 and a focus adjustment mechanism 32.

The composition adjustment mechanism 30 includes a casing 34 that holds the imaging element 14 and the lens 16, and an actuator 36 that moves the casing 34 in an extending direction of the optical axis LA. By adjusting the position of the casing 34 by the actuator 36, the angle of view is adjusted, that is, the size of the dentition to be formed on the imaging element 14 is adjusted. Note that the composition adjustment mechanism 30 automatically adjusts the position of the casing 34 such that, for example, the entire one tooth appears in the captured image. In addition, the composition adjustment mechanism 30 adjusts the position of the casing 34 so that the angle of view desired by the user is obtained on the basis of the operation by the user.

The focus adjustment mechanism 32 is held in the casing 34 of the composition adjustment mechanism 30 and includes a lens holder 38 that holds the lens 16, and an actuator 40 that moves the lens holder 38 in the extending direction of the optical axis LA. By the actuator 40 adjusting the relative position of the lens holder 38 with respect to the imaging element 14, the focus is adjusted. The focus adjustment mechanism 32 automatically adjusts the position of the lens holder 38 such that, for example, a tooth located at the center of the captured image is in focus. In addition, the focus adjustment mechanism 32 adjusts the position of the lens holder 38 on the basis of the operation by the user.

Components of the imaging optical system 12 except the mirror 18 may be provided in a handle portion 10b of the intraoral camera 10.

The imaging optical system of the intraoral camera 10 in the dentition image capturing system has been described above. A configuration of the dentition image capturing system will be described below.

Figure 3:
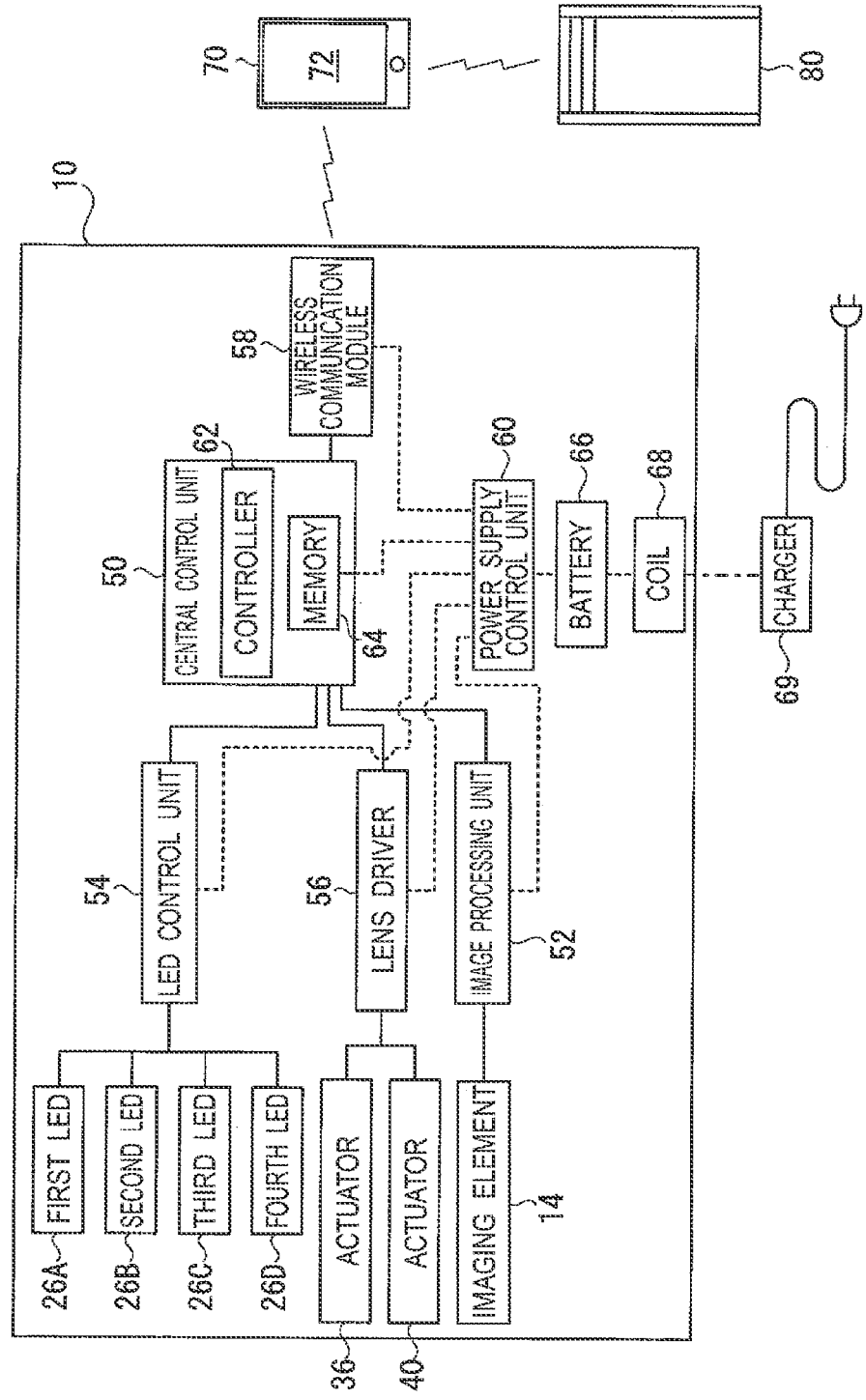
FIG. 3 is a schematic configuration diagram of the dentition image capturing system according to the first embodiment of the present disclosure.

FIG. 3 is a schematic configuration diagram of the dentition image capturing system according to the first embodiment of the present disclosure.

As illustrated in FIG. 3, a dentition image capturing system 100 according to the first embodiment is schematically configured to capture an image of a dentition using the intraoral camera 10 and execute image processing on the captured image.

As illustrated in FIG. 3, in the first embodiment, the dentition image capturing system 100 includes the intraoral camera 10, a mobile terminal 70, and a cloud server 80. The mobile terminal 70 is, for example, a wireless communicable mobile phone including a touch screen 72 capable of displaying, for example, a dentition image as an input device and an output device. The mobile terminal 70 functions as a user interface of the dentition image capturing system 100. The cloud server 80 is a server capable of communicating with the mobile terminal 70 via the Internet, or the like, and provides application for using the intraoral camera 10 to the mobile terminal 70. For example, the user downloads application from the cloud server 80 and installs the application in the mobile terminal 70. Further, the cloud server 80 acquires the dentition image captured by the intraoral camera 10 through the mobile terminal 70.

The dentition image capturing system 100 includes a central control unit 50 as a main part that controls the system, an image processing unit 52 that performs image processing on the dentition image from the imaging element 14, an LED control unit 54 that controls the plurality of LEDs 26A to 26D, and a lens driver 56 that controls the actuator 36 of the composition adjustment mechanism 30 and the actuator 40 of the focus adjustment mechanism 32.

The dentition image capturing system 100 includes a wireless communication module 58 that performs wireless communication with the mobile terminal 70 and a power supply control unit 60 that supplies power to the central control unit 50, and the like.

In the first embodiment, the central control unit 50 of the dentition image capturing system 100 is mounted on the handle portion 10b of the intraoral camera 10. For example, the central control unit 50 includes a controller 62 such as a CPU and an MPU that executes various kinds of processing which will be described later, and a memory 64 such as a RAM and a ROM that stores a program for causing the controller 62 to execute various kinds of processing. Note that in addition to the program, the memory 64 stores a dentition image (data) captured by the imaging element 14, various kinds of setting data, and the like.

In a case of the first embodiment, the image processing unit 52 is mounted on the handle portion 10b of the intraoral camera 10, acquires a dentition image (data) captured by the imaging element 14 on the basis of a control signal from the controller 62 of the central control unit 50, executes image processing on the acquired dentition image, and outputs the dentition image subjected to the image processing to the central control unit 50. The image processing unit 52 is constituted with, for example, a circuit and executes image processing such as noise removal and automatic white balance (AWB) processing on the dentition image, for example. The controller 62 transmits the dentition image output from the image processing unit 52 to the mobile terminal 70 via the wireless communication module 58. The mobile terminal 70 displays the transmitted dentition image on the touch screen 72, thereby presenting the dentition image to the user.

In a case of the first embodiment, the LED control unit 54 is mounted on the handle portion 10b of the intraoral camera 10 and turns on and off the first to fourth LEDs 26A to 26D on the basis of a control signal from the controller 62. The LED control unit 54 is constituted with, for example, a circuit. For example, when the user performs operation to activate the intraoral camera 10 on the touch screen 72 of the mobile terminal 70, a corresponding signal is transmitted from the mobile terminal 70 to the controller 62 via the wireless communication module 58. On the basis of the received signal, the controller 62 transmits a control signal to the LED control unit 54 to turn on the first to fourth LEDs 26A to 26D.

In a case of the present embodiment, the lens driver 56 is mounted on the handle portion 10b of the intraoral camera 10 and controls the actuator 36 of the composition adjustment mechanism 30 and the actuator 40 of the focus adjustment mechanism 32 on the basis of the control signal from the controller 62 of the central control unit 50. The lens driver 56 is constituted with, for example, a circuit. For example, when the user performs operation related to composition adjustment or focus adjustment on the touch screen 72 of the mobile terminal 70, a corresponding signal is transmitted from the mobile terminal 70 to the central control unit 50 via the wireless communication module 58. The controller 62 of the central control unit 50 transmits a control signal to the lens driver 56 so as to perform composition adjustment and focus adjustment on the basis of the received signal. In addition, for example, the controller 62 calculates control amounts of the actuators 36 and 40 necessary for composition adjustment and focus adjustment on the basis of the dentition image from the image processing unit 52 and transmits a control signal corresponding to the calculated control amounts to the lens driver 56.

In the present embodiment, the wireless communication module 58 is mounted on the handle portion 10b of the intraoral camera 10 and performs wireless communication with the mobile terminal 70 on the basis of the control signal from the controller 62. The wireless communication module 58 performs wireless communication with the mobile terminal 70 in accordance with existing communication standards such as WiFi and Bluetooth. Through the wireless communication module 58, the intraoral camera 10 transmits a dentition image of the tooth D to the mobile terminal 70, and the mobile terminal 70 transmits an operation signal to the intraoral camera 10.

In the present embodiment, the power supply control unit 60 is mounted on the handle portion 10b of the intraoral camera 10 and distributes power of a battery 66 to the central control unit 50, the image processing unit 52, the LED control unit 54, the lens driver 56, and the wireless communication module 58. The power supply control unit 60 is constituted with, for example, a circuit. In the present embodiment, the battery 66 is a rechargeable secondary battery and is wirelessly charged by an external charger 69 connected to a commercial power source via a coil 68 mounted on the intraoral camera 10.

The configuration of the dentition image capturing system 100 has been described above. Capturing of a dentition image to be performed by the dentition image capturing system 100 will be described below.

Figure 4:
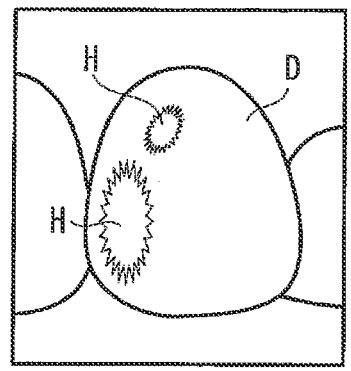
FIG. 4 is a view illustrating an example of a dentition image in a state where halation occurs on a surface of a tooth.

FIG. 4 is an example of a dentition image in a state where halation occurs on the surface of the tooth.

As illustrated in the dentition image of the example of FIG. 4, halation H can occur on the surface of the tooth D due to illumination light from the first to fourth LEDs 26A to 26D as a result of saliva or wetness on the surface of the tooth D. A surface portion of the tooth D where the halation H has occurred is unclear, and the state thereof cannot be confirmed. Thus, the dentition image capturing system 100 according to the first embodiment is configured to be able to create the dentition image in which the halation H has been removed.

In order to create the dentition image in which the halation H has been removed, the dentition image capturing system 100 is configured to capture a plurality of necessary dentition images.

Figure 5:
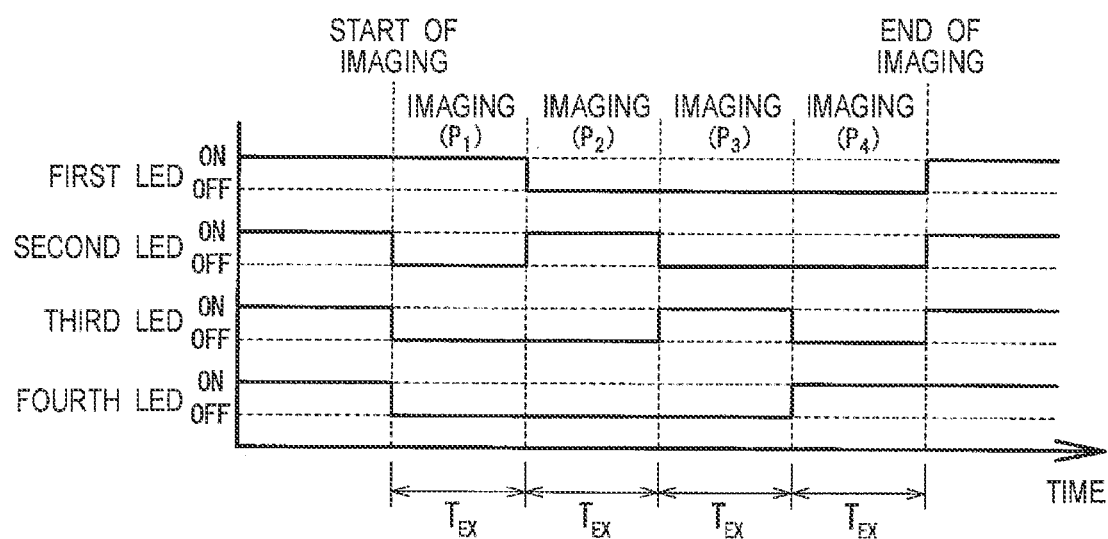
FIG. 5 is a timing chart of operation of capturing a plurality of dentition images necessary for creating a dentition image in which halation has been removed.
Figure 6:
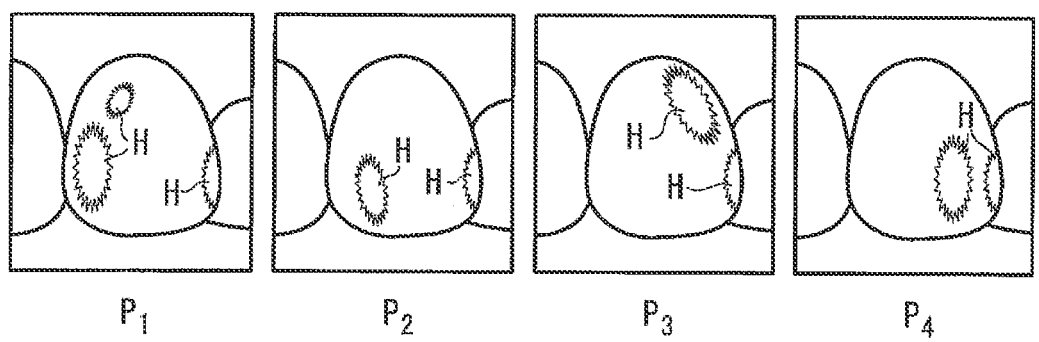
FIG. 6 is a view illustrating a plurality of dentition images obtained by the image capturing operation illustrated in FIG. 5.

FIG. 5 is a timing chart of operation of capturing a plurality of dentition images necessary for creating the dentition image in which the halation has been removed. FIG. 6 illustrates a plurality of dentition images obtained by the image capturing operation illustrated in FIG. 5.

As illustrated in FIGS. 5 and 6, the plurality of dentition images $P_1$ to $P_4$ are respectively captured under different illumination conditions. In addition, the plurality of dentition images $P_1$ to $P_4$ are captured in a predetermined exposure period $T_{EX}$.

For example, the user first holds the intraoral camera 10 with one hand and holds the mobile terminal 70 with the other hand. Next, in a state where the first to fourth LEDs 26A to 26D are turned on, the user adjusts the position of the head portion 10a of the intraoral camera 10 such that the tooth D to be captured appears on the touch screen 72 of the mobile terminal 70. For example, as illustrated in FIG. 2, the head portion 10a of the intraoral camera 10 is brought into contact with the gum G in the vicinity of the tooth D to be captured, thereby fixing the intraoral camera 10 in the oral cavity. After the position adjustment, the user performs operation related to start of imaging on the touch screen 72. On the basis of the operation, an imaging start signal is transmitted from the mobile terminal 70 to the central control unit 50 of the intraoral camera 10.

In a case of the first embodiment, the controller 62 of the central control unit 50 controls the LED control unit 54 to sequentially turn on the first to fourth LEDs 26A to 26D one by one. As illustrated in FIG. 5, when the first dentition image $P_1$ is captured, the first LED 26A is turned on (ON), and the remaining LEDs are turned off (OFF). When the central control unit 50 acquires the first dentition image $P_1$ (when it is stored in the memory 64), the second LED 26B is turned on and the remaining LEDs are turned off in order to capture the second dentition image $P_2$. After the second dentition image $P_2$ is acquired, the third LED 26C is turned on, the remaining LEDs are turned off, and the third dentition image $P_3$ is captured. Then, after the third dentition image $P_3$ is acquired, the fourth LED 26D is turned on, the remaining LEDs are turned off, and the fourth dentition image $P_4$ is captured. As a result, a plurality of dentition images $P_1$ to $P_4$ having different illumination conditions, specifically different illumination directions, and having substantially the same composition are captured (stored) in the predetermined exposure period $T_{EX}$. Thereafter, the controller 62 returns the first to fourth LEDs 26A to 26D to a state before imaging is started via the LED control unit 54 and notifies the user of the end of imaging via the mobile terminal 70.

As illustrated in FIG. 6, when the plurality of (four in a case of the present embodiment) dentition images $P_1$ to $P_4$ with substantially the same composition and captured in different illumination directions in the predetermined exposure period $T_{EX}$ are acquired, the controller 62 of the central control unit 50 executes processing of removing the halation H of the dentition image $P_1$. The processing will be described with reference to FIG. 7.

Figure 7:
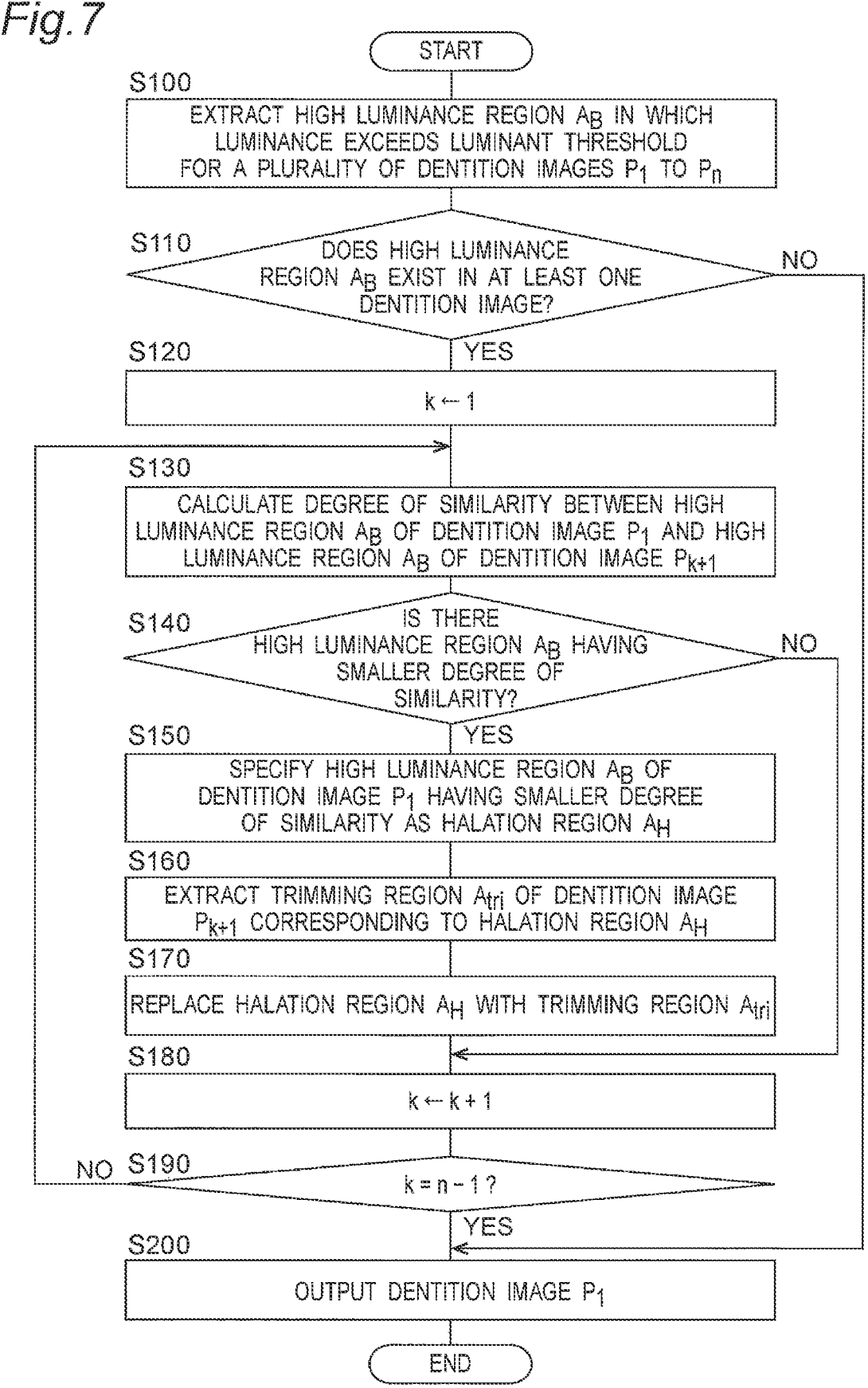
FIG. 7 is a flowchart of an example illustrating flow of halation removal processing.

FIG. 7 is a flowchart of an example illustrating flow of halation removal processing.

First, in step S100, the controller 62 extracts a high luminance region $A_B$ where luminance exceeds a predetermined luminance threshold in each of the plurality of dentition images $P_1$ to $P_n$ (in a case of the first embodiment, n=4). In other words, the controller 62 operates in accordance with a program stored in the memory 64 to function as a high luminance region extraction unit of the dentition image capturing system 100. The predetermined luminance threshold is, for example, experimentally or theoretically obtained in advance and is a value near luminance of the surface portion of the tooth where specular reflection has occurred.

Figure 8:
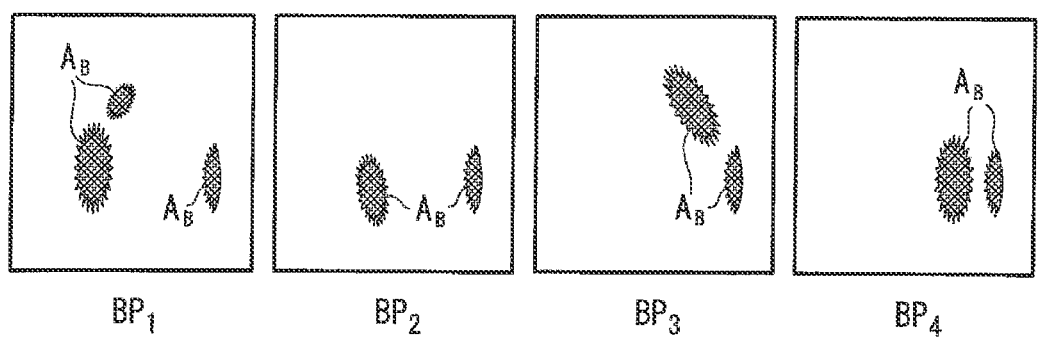
FIG. 8 is a view illustrating a plurality of luminance distribution images indicating extracted high luminance regions.

FIG. 8 is a view illustrating a plurality of luminance distribution images indicating the extracted high luminance regions.

As illustrated in FIG. 8, each of the plurality of luminance distribution images $BP_1$ to $BP_4$ indicates the extracted high luminance regions $A_B$ (cross hatching). The luminance distribution image $BP_1$ corresponds to the dentition image $P_1$, $BP_2$ corresponds to $P_2$, $BP_3$ corresponds to $P_3$, and $BP_4$ corresponds to $P_4$.

In step S110 subsequent to step S100, it is determined whether or not the high luminance regions $A_B$ exist in all the plurality of dentition images. In a case where the high luminance region $A_B$ exists in at least one of the dentition images, the processing proceeds to step S120. Otherwise, that is, in a case where the high luminance regions $A_B$ do not exist in all the dentition images, the processing proceeds to step S200.

In step S120, the controller 62 sets a parameter k to 1.

In step S130, the controller 62 calculates a degree of similarity that is a number indicating the degree of similarity between the high luminance region $A_B$ of the dentition image $P_1$ and the high luminance region $A_B$ of the dentition image $P_{k+1}$. In other words, the controller 62 operates in accordance with the program stored in the memory 64 to function as a high luminance region comparison unit of the dentition image capturing system 100.

The degree of similarity of the high luminance regions $A_B$ is calculated using, for example, template matching. Examples of the template matching include a sum of squared difference (SSD), a sum of absolute difference (SAD), and normalized cross-correlation (NCC).

In a case of using the SSD, the sum of squares of differences in the luminance values of the pixels of the luminance distribution images $BP_1$ and $BP_{k+1}$ corresponding to the dentition images $P_1$ and $P_{k+1}$, respectively, is calculated using the following Equation 1. A reciprocal of the calculated value $R_{SSD}$ is set as the degree of similarity between the high luminance regions.

[Math. 1]

$$R_{SSD} = \sum_{j=0}^{N-1}\sum_{i=0}^{M-1} (I(i, j) - T(i, j))^2 \quad \text{(Equation 1)}$$

In Equation 1, T(i, j) is a luminance value of a pixel of the luminance distribution image $BP_1$ corresponding to the dentition image $P_1$, and I(i, j) is a luminance value of a pixel of the luminance distribution image $BP_{k+1}$ corresponding to the dentition image $P_{k+1}$.

In a case of using the SAD, the sum of the absolute values of the differences in the luminance values of the pixels of the luminance distribution images $BP_1$ and $BP_{k+1}$ respectively corresponding to the dentition image $P_1$ and $P_{k+1}$ is calculated using the following Equation 2. A reciprocal of the calculated value $R_{SAD}$ is set as the degree of similarity between the high luminance regions.

[Math. 2]

$$R_{SAD} = \sum_{j=0}^{N-1}\sum_{i=0}^{M-1} |I(i, j) - T'i, j)| \quad \text{(Equation 2)}$$

In Equation 2, T(i, j) is a luminance value of a pixel of the luminance distribution image $BP_1$ corresponding to the dentition image $P_1$, and I(i, j) is a luminance value of a pixel of the luminance distribution image $BP_{k+1}$ corresponding to the dentition image $P_{k+1}$.

In a case of using the NCCC, normalized cross-correlation of the luminance values of the pixels of the luminance distribution images $BP_1$ and $BP_{k+1}$ respectively corresponding to the dentition image $P_1$ and $P_{k+1}$ is evaluated using the following Equation 3. An evaluation value $R_{NCC}$ calculated using Equation 3 is a numerical value in a range of −1.0 to +1.0, where a numerical value closer to +1.0 indicates a higher degree of similarity.

[Math. 3]

$$R_{NCC} = \frac{\sum_{j=0}^{N-1}\sum_{i=0}^{M-1} I(i, j)T(i, j)}{\sqrt{\sum_{j=0}^{N-1}\sum_{i=0}^{M-1} I(i, j)^2 \times \sum_{j=0}^{N-1}\sum_{i=0}^{M-1} T(i, j)^2}} \quad \text{(Equation 3)}$$

In Equation 3, T(i, j) is a luminance value of a pixel of the luminance distribution image $BP_1$ corresponding to the dentition image $P_1$, and I(i, j) is a luminance value of a pixel of the luminance distribution image $BP_{k+1}$ corresponding to the dentition image $P_{k+1}$.

When the degree of similarity between the high luminance region $A_B$ of the dentition image $P_1$ and the high luminance region $A_B$ of the dentition image $P_{k+1}$ is calculated in step S130, the controller 62 determines whether or not the high luminance region $A_B$ having the degree of similarity smaller than a predetermined similarity threshold exists in the dentition image $P_1$ in step S140. In a case where the high luminance region $A_B$ having the degree of similarity smaller than the predetermined similarity threshold exists in the detention image $P_1$, the processing proceeds to step S150. Otherwise, the processing proceeds to step S170.

Figure 9:
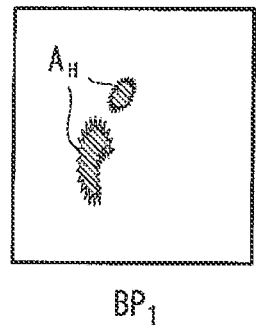
FIG. 9 is a view illustrating a luminance distribution image illustrating a high luminance region having a degree of similarity smaller than a predetermined similarity threshold.

FIG. 9 illustrates a luminance distribution image indicating a high luminance region having a degree of similarity smaller than the predetermined similarity threshold.

As illustrated in FIG. 9, in the luminance distribution image $BP_1$ corresponding to the dentition image $P_1$, in a case where there is a high luminance region (diagonal hatching) in which the degree of similarity is smaller than the predetermined similarity threshold, in step S150, the controller 62 specifies the region as a region AH (halation region) in which halation occurs in the dentition image $P_1$. In other words, the controller 62 operates in accordance with the program stored in the memory 64 to function as a halation region specification unit of the dentition image capturing system 100.

Figure 10:
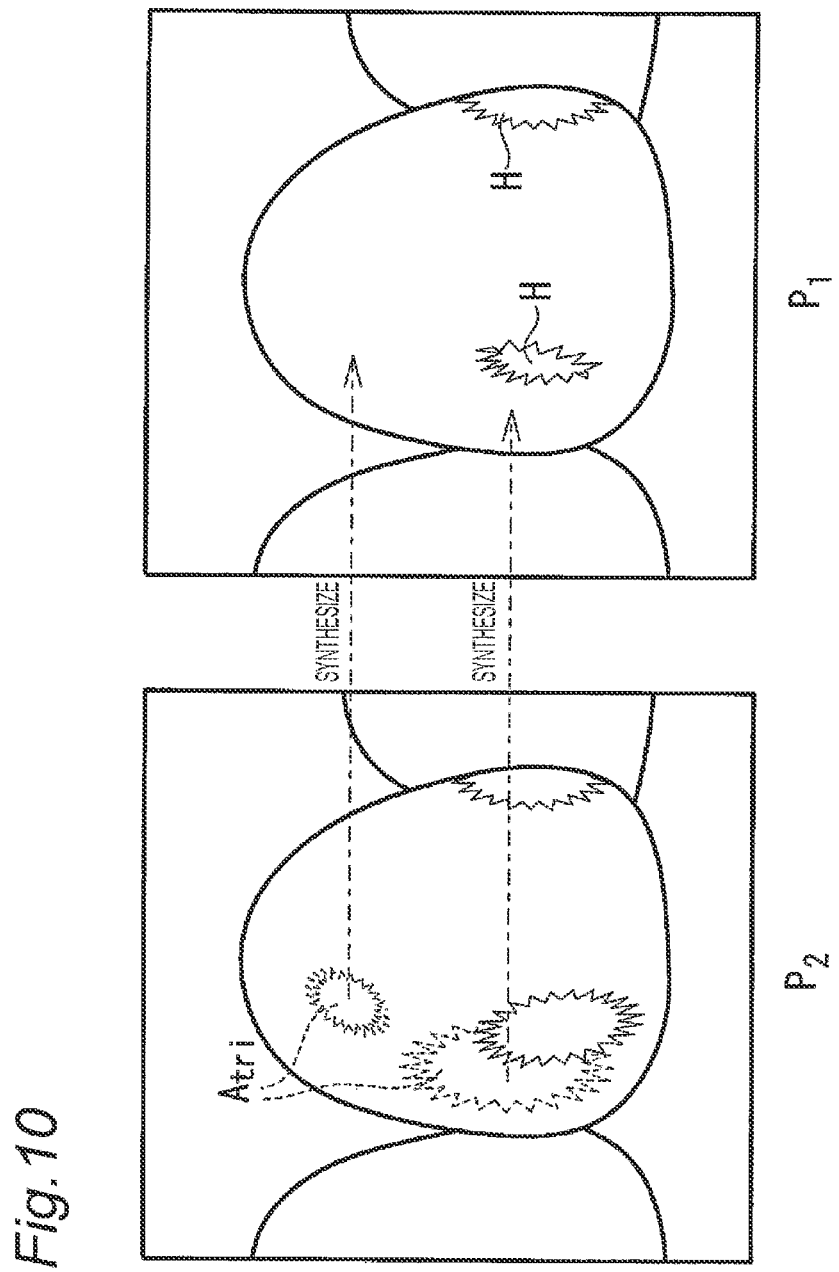
FIG. 10 is a view illustrating trimming processing and synthesis processing.
Figure 11:
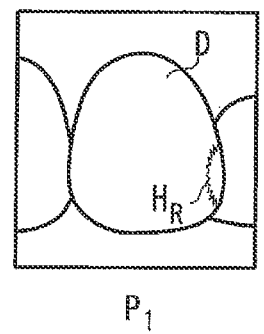
FIG. 11 is a view illustrating a dentition image from which halation has been removed.

FIG. 10 is a view illustrating trimming processing and synthesis processing. FIG. 11 illustrates the dentition image in which the halation is partially removed by the trimming processing and the synthesis processing.

In step S160, as illustrated in FIG. 10, the controller 62 extracts a region $A_{tri}$ (trimming region) of the dentition image $P_{k+1}$ corresponding to the halation region $A_H$ of the dentition image $P_1$. Then, in subsequent step S170, the controller 62 executes image synthesis processing of replacing the halation region $A_H$ of the dentition image $P_1$ with the trimming region $A_{tri}$ of the dentition image $P_{k+1}$. In other words, the controller 62 operates in accordance with the program stored in the memory 64 to function as a synthesis processing unit of the dentition image capturing system 100. As illustrated in FIG. 11, the dentition image $P_1$ in which part of the halation H has been removed is obtained by the processing in steps S160 and S170 (see FIG. 6).

In step S180, the controller 62 increments the parameter k by +1. In subsequent step S190, the controller 62 determines whether or not the parameter k is n−1. The parameter n is the number of dentition images. In a case where the parameter k is n−1 (k=3 in a case of the first embodiment), the processing proceeds to step S200. Otherwise, the processing returns to step S130.

By repeating the processing of steps S130 to S190, calculation of the degree of similarity and image synthesis processing of the high luminance regions $A_H$ (there may be a dentition image for which the image synthesis processing is not executed depending on a result of calculation of the degree of similarity) are executed between the dentition image $P_1$ and each of the other dentition images $P_2$ to $P_4$.

When calculation of the degree of similarity calculation and the image synthesis processing of the high luminance regions $A_H$ are executed between the dentition image $P_1$ and each of the other dentition images $P_2$ to $P_4$, in step S200, the controller 62 outputs (displays) the dentition image $P_1$ via the touch screen 72 of the mobile terminal 70. In other words, the touch screen 72 of the mobile terminal 70 functions as a dentition image output unit of the dentition image capturing system 100. When the processing in step S200 ends, the halation removal processing is completed.

FIG. 11 illustrates the dentition image from which the halation has been removed.

As illustrated in FIG. 11, in the dentition image $P_1$, the halation H is removed except for part (see FIG. 6). The remaining halation $H_R$ is halation that occurs even when the illumination direction is changed. It can be estimated that the halation $H_R$ occurs by multiple reflection of the inlay packed in the tooth D. Thus, the halation removal processing is not executed on the halation $H_R$, and inlay appears in the dentition image $P_1$.

In other words, the high luminance region $A_B$ of the dentition image $P_1$ in which the degree of similarity with each of the high luminance regions $A_B$ of the other dentition images $P_2$ to $P_4$ is greater than the predetermined similarity threshold is estimated as a region where an inlay can exist, and the region is left as it is without being subjected to the image synthesis processing. This results in preventing an unnatural situation where the inlay does not appear in the dentition image of the tooth D including the inlay.

Thus, as illustrated in FIG. 11, it is possible to obtain the dentition image from which the halation of the tooth portion except the inlay has been removed.

According to the first embodiment as described above, the image of the tooth can be clearly captured.

Second Embodiment

A dentition image capturing system according to the second embodiment is an improved form of the dentition image capturing system according to the first embodiment described above and is particularly suitable for capturing a dentition image including a tooth having an inlay. Thus, the second embodiment will be described focusing on different points.

When an image of a dentition including a tooth having an inlay, particularly a dentition including a tooth having a metal inlay is captured, part of the inlay may be specularly reflected. In the specularly reflected inlay portion, pixels of the corresponding imaging element may be saturated and whiteout may occur, so that the state cannot be confirmed.

Figure 12:
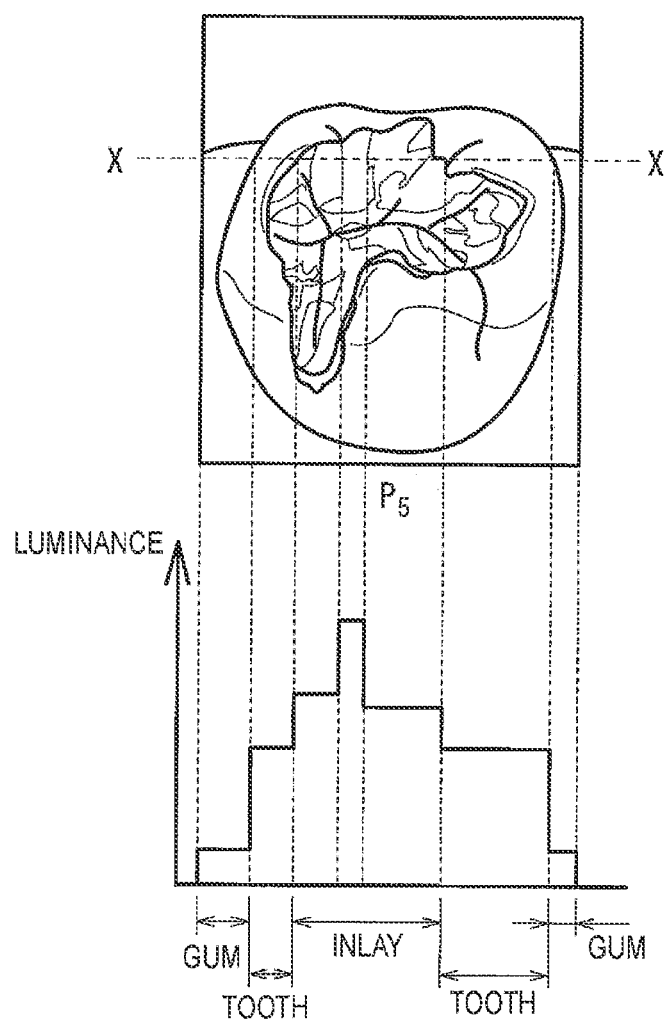
FIG. 12 is a view illustrating a dentition image including a tooth including an inlay and luminance distribution thereof.

FIG. 12 illustrates a dentition image including a tooth having an inlay and luminance distribution thereof.

The luminance distribution illustrated in FIG. 12 indicates luminance distribution on a line X-X that sequentially passes through the gum, the tooth, the inlay, the tooth, and the gum in the tooth image $P_5$. Luminance of the gum is the lowest, and luminance of the inlay is the highest. A portion having higher luminance than other portions also exists in the inlay, and it is estimated that specular reflection occurs in this inlay portion. Thus, by reducing the luminance of the inlay, which is higher in luminance than the gum and the tooth, it is possible to prevent occurrence of whiteout in the tooth including the inlay, so that it is possible to obtain a dentition image in which the entire tooth clearly appears.

In order to reduce the luminance of the inlay, in a case of the second embodiment, an exposure period of the plurality of dentition images necessary for the halation removal processing as illustrated in FIG. 6 is shortened from the predetermined exposure period $T_{EX}$. Specifically, before capturing a plurality of dentition images necessary for the halation removal processing, the dentition image capturing system according to the second embodiment executes the following calibration processing.

Figure 13:
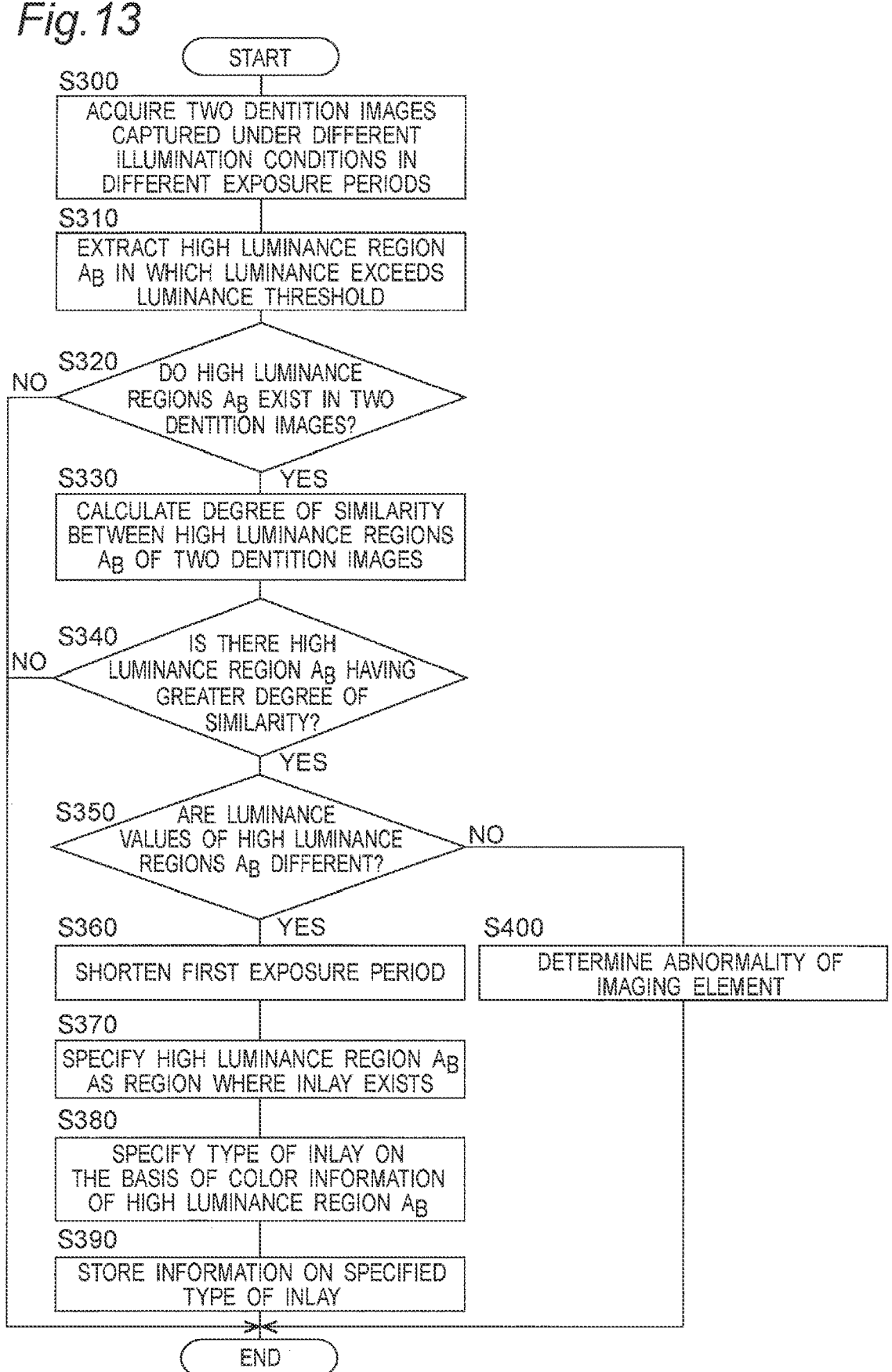
FIG. 13 is a flowchart illustrating flow of calibration processing.

FIG. 13 is a flowchart illustrating flow of the calibration processing.

As illustrated in FIG. 13, in step S300, the controller 62 acquires two dentition images for calibration processing from the imaging element 14. In this event, the two dentition images are captured with different exposure periods under different illumination conditions. Note that both of these exposure periods may be different from the predetermined exposure period $T_{EX}$, or one of them may be the same. One dentition image is captured, for example, in a state where only the first LED 26A is turned on. The other dentition images are captured, for example, in a state where only the third LED 26C is turned on.

In step S310, the controller 62 extracts a high luminance region $A_B$ exceeding the predetermined luminance threshold in each of the two dentition images.

In step S320, the controller 62 determines whether or not the high luminance regions $A_B$ exist in the two dentition images. In a case where the high luminance regions $A_B$ exist in the two dentition images, the processing proceeds to step S330. Otherwise, a probability that whiteout occurs in the tooth when the plurality of dentition images necessary for the halation removal processing is captured is low, and thus, the calibration processing is ended.

In step S330, the controller 62 calculates the degree of similarity between the high luminance regions $A_B$ of the two dentition images.

In step S340, the controller 62 determines whether or not there is a high luminance region $A_B$ having a degree of similarity greater than the predetermined similarity threshold. In a case where there is a high luminance region $A_B$ having a degree of similarity greater than the predetermined similarity threshold, the processing proceeds to step S350. Otherwise, there is a high possibility that an inlay does not exist, and thus, the calibration processing is ended.

In step S350, the controller 62 determines whether or not the luminance values of the high luminance regions $A_B$ of the two dentition images are different from each other. In a case where the luminance values are different from each other, the processing proceeds to step S360. Otherwise, the processing proceeds to step S400, and the controller 62 determines that an abnormality has occurred in the imaging element 14. In other words, the controller 62 functions as an imaging device abnormality determination unit of the dentition image capturing system. The reason why such abnormality determination can be executed is that the luminance values of the high luminance regions $A_B$ are not different and are the same although the two dentition images are captured in different exposure periods. In order to perform abnormality determination of the imaging element with high accuracy, it is preferable that a difference between the exposure periods of the two dentition images is large.

In step S360, the controller 62 shortens the predetermined exposure period $T_{EX}$ when the plurality of dentition images necessary for the halation removal processing is captured. In other words, the high luminance region $A_B$ having a high degree of similarity and with different luminance values is a region where there is a high possibility that an inlay where specular reflection is likely to occur exists. Thus, in order to prevent whiteout in the inlay included in the plurality of dentition images necessary for the halation removal processing, the predetermined exposure period $T_{EX}$ is shortened.

In step S370, the controller 62 specifies the high luminance region $A_B$ having a high degree of similarity and with different luminance values as the region where the inlay exists. In subsequent step S380, the controller 62 specifies the type of the inlay on the basis of color information (information that can be acquired from the dentition image such as color and gloss) of the high luminance region $A_B$ specified as the region where the inlay exists. Thus, the color information such as color and gloss of various types of inlays prepared in advance is stored in the memory 64. With reference to the information in the memory 64, the controller 62 specifies the type of the inlay in the high luminance region $A_B$.

In step S390, the controller 62 stores information on the specified type of the inlay in the memory 64. As illustrated in FIG. 11, when the inlay appears in the dentition image from which the halation has been removed, the information on the type of the inlay is output together with the dentition image.

According to the second embodiment as described above, in a similar manner to the first embodiment, the image of the tooth can be clearly captured. In particular, the image of the tooth including the inlay can be clearly captured.

Although the present disclosure has been described above with reference to the first and second embodiments, the embodiments of the present disclosure are not limited to the embodiments described above.

For example, in a case of the above embodiments, the halation removal processing is executed for one tooth, but the embodiments of the present disclosure are not limited thereto. It is also possible to simultaneously perform halation removal processing on a plurality of teeth. For this purpose, the intraoral camera may include, for example, a 360 degree camera. Furthermore, for example, the head portion 10a of the intraoral camera 10 illustrated in FIG. 1 may be configured to be rotatable by 360 degrees with respect to the neck portion 10c so as to acquire a panoramic dentition image.

In addition, in a case of the first embodiment, only one of the first to fourth LEDs 26A to 26D, which are illumination devices that respectively irradiate the tooth to be captured with light from different directions, is turned on when one dentition image is captured as illustrated in FIG. 5, but the embodiments of the present disclosure are not limited thereto. For example, an illumination condition in which two or more illumination devices are turned on may be provided as the illumination conditions for capturing one dentition image. In addition, an illumination condition in which all the illumination devices radiate light or an illumination condition in which all the illumination devices are turned off may be provided. This can increase illumination conditions at the time of imaging of the tooth, so that it is possible to increase a plurality of dentition images having different illumination conditions necessary for the halation removal processing. Use of a large number of dentition images improves accuracy of the halation removal processing.

Concerning the illumination device, as illustrated in FIG. 5, the first to fourth LEDs 26A to 26D are controlled to be turned on/off, but the embodiments of the present disclosure are not limited thereto. The illumination device may be, for example, an illumination device for which a light amount is adjustable. Use of the illumination device for which the light amount is adjustable can further increase illumination conditions at the time of imaging of the tooth, so that it is possible to increase a plurality of dentition images having different illumination conditions necessary for the halation removal processing. Use of a large number of dentition images improves accuracy of halation removal.

Regarding the light amount adjustment of the illumination device, the light amount of the illumination device may be automatically or manually adjusted before capturing a plurality of dentition images having different illumination conditions necessary for the halation removal processing. For example, illuminance around the incidence port of the intraoral camera may be measured using an illuminance sensor, and the light amount of the illumination device may be adjusted on the basis of the measurement result. Furthermore, for example, a distance from the intraoral camera to the tooth to be captured may be measured using a distance measuring sensor, and the light amount of the illumination device may be adjusted on the basis of the measurement result. Further, for example, the user may adjust the light amount of the illumination device through the touch screen 72 while confirming the dentition image through the touch screen 72 of the mobile terminal 70. By appropriately adjusting the light amount of the illumination device before capturing a plurality of dentition images having different illumination conditions necessary for the halation removal processing, it is possible to acquire a plurality of dentition images in which occurrence of halation is prevented to some extent. Use of the plurality of dentition images in which occurrence of halation is prevented to some extent improves accuracy of halation removal.

Regarding the irradiation light of each of the plurality of illumination devices, in a case of the first embodiment, all of the first to fourth LEDs 26A to 26D output white light. Alternatively, some illumination devices may radiate ultraviolet light. Radiation of ultraviolet light makes dental plaque clear in the dentition image. This enables plaque check using the dentition image.

In a case where the illumination device radiates ultraviolet light, the head portion 10a of the intraoral camera 10 may be sterilized by the ultraviolet light. In this case, a head cover that covers the entire head portion 10a is prepared. The inner surface of the head cover is mirror-finished. When the illumination device provided on the head portion 10a in a state of being covered with the head cover radiates ultraviolet light, the ultraviolet light is reflected by the inner surface of the mirror-finished head cover and is radiated on the head portion 10a. As a result, the head portion 10a is sterilized by the ultraviolet light.

With respect to the irradiation light of the illumination device, the intraoral camera 10, particularly, a portion of the head portion 10a and the neck portion 10c entering the oral cavity is preferably covered with a film (for example, black paint) having high light absorbency so as to prevent reflection of light. This prevents light reflected by the intraoral camera 10 from being projected onto the tooth, that is, prevents occurrence of halation.

In order to acquire a plurality of dentition images having different illumination conditions necessary for the halation removal processing in a better state, the user may adjust white balance of the dentition images. For example, the user may adjust white balance through the touch screen 72 of the mobile terminal 70 while checking the dentition image through the touch screen 72.

In order to acquire a plurality of dentition images having different illumination conditions necessary for the halation removal processing in a better state, the intraoral camera may be subjected to defogging treatment. The inside of the oral cavity has high humidity, and thus, there is a possibility that components of the imaging optical system 12 such as the imaging element 14 and the lens 16 may get wet by moisture. To address this, for example, a transmission surface of the lens 16 or a reflection surface of the mirror 18 may be subjected to water repellent treatment. Furthermore, for example, surrounding air may be warmed so that the imaging element 14, the lens 16, and the like, do not get wet (so that dew condensation does not occur). As a heat source for heating the air, a heater may be used. Alternatively, the air may be heated by exhaust heat from an electronic component that is driven by power being supplied from the battery 66. Alternatively, in a case where an unclear portion partially occurs in the dentition image, it may be determined that the lens 16 or the cover 28 gets wet, and the user may be notified of the fact.

In order to acquire a plurality of dentition images having different illumination conditions necessary for the halation removal processing in a better state, in a case of the first embodiment, as illustrated in FIG. 2, the head portion 10a of the intraoral camera 10 abuts on the gum G. Fixing of the position of the head portion 10a of the intraoral camera 10 in the oral cavity is not limited thereto. For example, the neck portion 10c may be provided with a seating surface such as a flat surface or a concave surface on which an upper lip or a lower lip is to be seated.

In order to acquire a plurality of dentition images having different illumination conditions necessary for halation removal processing in a better state, particularly, in order to facilitate imaging of back teeth or an outer surface close to the back teeth, a spacer may be provided in the intraoral camera 10.

Figure 14:
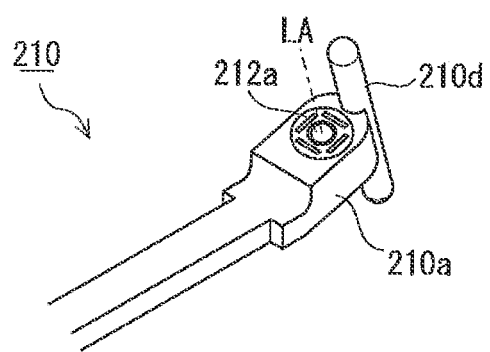
FIG. 14 is a perspective view of part of an intraoral camera in a dentition image capturing system according to another embodiment.

FIG. 14 is a perspective view of part of an intraoral camera in a dentition image capturing system according to another embodiment.

As illustrated in FIG. 14, a spacer 210d extending in the extending direction of the optical axis LA of the imaging optical system and having round both ends is provided in a head portion 210a of an intraoral camera 210. The spacer 210d is disposed between the gum near the back teeth and the inner portion of the cheek facing the gum, so that space is formed between the cheek and the outer surface of the back teeth. This results in securing a distance appropriate for imaging between the incidence port 212a of the imaging optical system and the outer surface of the back teeth. The spacer 210d is preferably attachable to and detachable from the head portion 210a in consideration of imaging of teeth other than the back teeth.

In a case where images of a plurality of teeth are captured, the dentition image capturing system may teach the user about the imaging procedure. For example, an intraoral image (for example, an illustration) including all teeth is displayed on the touch screen 72 of the mobile terminal 70, and the position of the tooth to be captured next by the user is taught using the intraoral image. When the user aligns the head portion 10a of the intraoral camera 10 with the taught tooth, the type of tooth, the imaging direction, the angle of view, and the like, are determined on the basis of the dentition image, and an appropriate imaging direction, angle of view, and the like, are taught to the user. When the imaging direction, the angle of view, and the like, are appropriately adjusted by the user, the intraoral camera 10 captures the image of the tooth. Note that the head portion 10a is configured to be rotatable with respect to the neck portion 10c, and a motor that rotates the head portion 10a is mounted on the intraoral camera 10, so that the imaging direction can be adjusted without intervention of the user. The type of the tooth can be specified by executing image recognition on the tooth image appearing in the dentition image. As a result, when the user aligns the head portion 10a with a tooth different from the tooth to be captured next, the user can be pointed out the mistake.

Finally, in a case of the first embodiment, the dentition image capturing system 100 includes a toothbrush-like intraoral camera 10 and the mobile terminal 70 as illustrated in FIGS. 1 and 3. In addition, the LEDs 26A to 26D as illumination devices, the imaging element 14 as an imaging device, the controller 62 that executes halation removal processing, and the like, are mounted on the intraoral camera 10. Then, the mobile terminal 70 outputs the dentition image. However, the embodiments of the present disclosure are not limited thereto.

For example, the controller that executes the halation removal processing may be in the mobile terminal. In other words, a CPU, an MPU, or the like, mounted on the mobile terminal executes halation removal processing of the dentition image. In addition, for example, a personal computer may be used instead of the mobile terminal, and the intraoral camera may be connected to the personal computer by USB, or the like.

In addition, the camera on which the illumination device and the imaging device are mounted and at least part of which enters the oral cavity is not limited to a toothbrush-like intraoral camera. A form of the camera is not limited as long as the portion provided with the incidence port of the illumination device or the imaging optical system can freely move in the oral cavity. For example, the imaging optical system including the imaging device and the illumination device may be mounted on the head portion of an electric toothbrush.

In other words, in a broad sense, the dentition image capturing system according to the embodiment of the present disclosure includes: a plurality of illumination devices configured to irradiate a tooth to be captured with light from different directions; an imaging device configured to capture first and second dentition images including the tooth under different illumination conditions of the plurality of illumination devices in a predetermined exposure period; a high luminance region extraction unit configured to extract a high luminance region in which luminance exceeds a predetermined luminance threshold for each of the first and second dentition images; a high luminance region comparison unit configured to calculate a degree of similarity indicating a degree of similarity between a high luminance region of the first dentition image and a high luminance region of the second dentition image; and a halation region specification unit configured to specify the high luminance region of the first dentition image as a halation region in a case where the degree of similarity is smaller than a predetermined similarity threshold; an image synthesis processing unit configured to extract a trimming region in the second dentition image corresponding to the halation region of the first dentition image and execute image synthesis processing of replacing the halation region with the trimming region; and a dentition image output unit configured to output the first dentition image subjected to image synthesis processing.

Further, in a broad sense, the dentition image capturing method according to the embodiment of the present disclosure is a dentition image capturing method for capturing a dentition image including a tooth to be captured, the method including: irradiating a tooth to be captured with light from different directions by a plurality of illumination devices; capturing first and second dentition images by the imaging device under different illumination conditions of the plurality of illumination devices in a predetermined exposure period; extracting a high luminance region in which luminance exceeds a predetermined luminance threshold for each of the first and second dentition images; calculating a degree of similarity indicating a degree of similarity between a high luminance region of the first dentition image and a high luminance region of the second dentition image; specifying the high luminance region of the first dentition image as a halation region in a case where the degree of similarity is smaller than a predetermined similarity threshold; extracting a trimming region in the second dentition image corresponding to the halation region and executing image synthesis processing of replacing the halation region with the trimming region; and outputting the first dentition image subjected to image synthesis processing.

As described above, the above embodiments have been described as examples of the technique in the present disclosure. Thus, the drawings and detailed description are provided. Thus, the components described in the drawings and the detailed description may include not only components essential for solving the problem but also components that are not essential for solving the problem in order to illustrate the above technique. Thus, it should not be immediately recognized that these non-essential components are essential on the basis of the fact that these non-essential components are described in the drawings and the detailed description.

In addition, the above embodiments are intended to illustrate the technique in the present disclosure, and thus, various changes, replacements, additions, omissions, and the like, can be made within the scope of the claims or equivalents thereof.

INDUSTRIAL APPLICABILITY

The present disclosure is applicable to an apparatus, a system, and a method for imaging a dentition and outputting a dentition image.

The invention claimed is:

1. A dentition image capturing system comprising:
a plurality of illumination devices configured to irradiate a tooth to be captured with light from different directions;
an imaging device configured to capture first and second dentition images including the tooth under different illumination conditions of the plurality of illumination devices in a predetermined exposure period;
a high luminance region extraction unit configured to extract a high luminance region in which luminance exceeds a predetermined luminance threshold for each of the first and second dentition images;
a high luminance region comparison unit configured to calculate a degree of similarity indicating a degree of similarity between a high luminance region of the first dentition image and a high luminance region of the second dentition image;
a halation region specification unit configured to specify the high luminance region of the first dentition image as a halation region in a case where the degree of similarity is smaller than a predetermined similarity threshold;
an image synthesis processing unit configured to extract a trimming region in the second dentition image corresponding to the halation region of the first dentition image and execute image synthesis processing of replacing the halation region with the trimming region; and
a dentition image output unit configured to output the first dentition image subjected to image synthesis processing.

2. The dentition image capturing system according to claim 1, wherein in a case where neither the first dentition image nor the second dentition image includes a high luminance region, the dentition image output unit outputs the first dentition image.

3. The dentition image capturing system according to claim 1, wherein
the imaging device captures third and fourth dentition images under different illumination conditions in exposure periods different from each other,
the high luminance region extraction unit extracts high luminance regions of the third and fourth dentition images,
the high luminance region comparison unit calculates a degree of similarity between the high luminance region of the third dentition image and the high luminance region of the fourth dentition image, and
in a case where the degree of similarity between the high luminance region of the third dentition image and the high luminance region of the fourth dentition image is greater than the predetermined similarity threshold, the imaging device captures the first and second dentition images in an exposure period that is made shorter than the predetermined exposure period.

4. The dentition image capturing system according to claim 3, further comprising an imaging device abnormality determination unit configured to determine that an abnormality occurs in the imaging device in a case where luminance values of the high luminance regions of the third and fourth dentition images are same.

5. The dentition image capturing system according to claim 1, further comprising an inlay type specification unit configured to specify a high luminance region having a degree of similarity greater than the predetermined similarity threshold as a region where an inlay exists and specify a type of the inlay on a basis of color information of the high luminance region and color information of a plurality of types of inlays prepared in advance.

6. The dentition image capturing system according to claim 1, wherein the illumination devices and the imaging device are incorporated into a toothbrush-like casing.

7. The dentition image capturing system according to claim 6, wherein the dentition image output unit is a mobile terminal including a screen capable of displaying a dentition image.

8. A dentition image capturing method for capturing a dentition image including a tooth to be captured, the method comprising:
irradiating a tooth to be captured with light from different directions by a plurality of illumination devices;
capturing first and second dentition images including the tooth by the imaging device under illumination conditions of the plurality of illumination devices in a predetermined exposure period;
extracting a high luminance region in which luminance exceeds a predetermined luminance threshold for each of the first and second dentition images; and
calculating a degree of similarity indicating a degree of similarity between a high luminance region of the first dentition image and a high luminance region of the second dentition image;
specifying the high luminance region of the first dentition image as a halation region in a case where the degree of similarity is smaller than a predetermined similarity threshold;
extracting a trimming region in the second dentition image corresponding to the halation region;
executing image synthesis processing of replacing the halation region with the trimming region; and
outputting the first dentition image subjected to image synthesis processing.

* * * * *